United States Patent
Asher et al.

(10) Patent No.: US 6,187,599 B1
(45) Date of Patent: *Feb. 13, 2001

(54) POLYMERIZED CRYSTALLINE COLLOIDAL ARRAYS

(75) Inventors: Sanford A. Asher; John H. Holtz, both of Pittsburgh, PA (US)

(73) Assignee: University of Pittsburgh, Pittsburgh, PA (US)

(*) Notice: Under 35 U.S.C. 154(b), the term of this patent shall be extended for 0 days.

This patent is subject to a terminal disclaimer.

(21) Appl. No.: 09/111,610

(22) Filed: Jul. 7, 1998

Related U.S. Application Data

(63) Continuation of application No. 08/819,240, filed on Mar. 17, 1997, now Pat. No. 5,854,078, which is a continuation-in-part of application No. 08/743,816, filed on Nov. 6, 1996, now Pat. No. 5,898,004.

(51) Int. Cl.[7] ........................ G01N 33/545; G01N 33/66; G01J 3/18
(52) U.S. Cl. .................... 436/531; 252/582; 359/885; 435/14; 436/73; 436/79; 436/518; 436/529
(58) Field of Search ..................... 436/531, 73, 518, 436/529, 79; 252/582; 359/885; 435/14

(56) References Cited

U.S. PATENT DOCUMENTS

| | | | |
|---|---|---|---|
| 4,627,689 | 12/1986 | Asher | 350/362 |
| 4,632,517 | 12/1986 | Asher | 350/362 |
| 5,200,051 | 4/1993 | Cozette et al. | |
| 5,226,902 | 7/1993 | Bae et al. | 604/892.1 |
| 5,274,018 | 12/1993 | Tanaka et al. | 524/166 |
| 5,281,370 | 1/1994 | Asher et al. | 264/1.1 |
| 5,330,685 | 7/1994 | Panzer et al. | 252/582 |
| 5,338,492 | 8/1994 | Panzer et al. | 252/582 |
| 5,342,552 | 8/1994 | Panzer et al. | 252/582 |
| 5,368,781 | 11/1994 | Haacke et al. | |
| 5,536,834 | 7/1996 | Singh et al. | 544/98 |
| 5,674,521 | * 10/1997 | Gehrke et al. | 424/423 |
| 5,898,004 | * 4/1999 | Asher et al. | 436/518 |

OTHER PUBLICATIONS

J. H. Holtz et al., "Intelligent Polymerized Crystalline Colloid Arrays: Novel Chemical Sensor Materials", *Analytical Chemistry*, vol. 70, No. 4, pp. 780–791 (1998).

J. H. Holtz et al., "Polymerized Colloidal Crystal Hydrogel Films, as Intelligent Chemical Sensing Materials", *Nature*, vol. 389, pp. 829–832 (1997).

J. M. Jethmalani et al. *Chem. Mater.*, vol. 8, pp. 2138–2146 (1996).

Kikuchi, et al., "Glucose–Sensing Electrode Coated with Polymer Complex Gel Containing Phenylboronic Acid", *Anal. Chem.*, vol. 68, pp. 823–828 (1996).

H.B. Sunkara et al., *Polym. Prepr.*, vol. 37, pp. 453–454 (1996).

A. Suzuki et al., *Chem. Abstr.*, vol. 125, 134841K (1996).

W.C. Mitchie et al., *Opt. Lett*, vol. 20, pp. 103–105 (1995).

Schalkhammer et al., "The Use of Metal–island–coated pH–Sensitive Swelling Polymers for Biosensor Applications," *Sensors and Actuators B*, vol. 24–25, pp. 166–172 (1995).

Sheppard et al., "Microfabricated Conductimetric pH Sensor", *Sensors and Actuators B*, vol. 28, pp. 95–102 (1995).

M. Stoimenova et al., *J. colloid Interface Sci.*, vol. 176, pp. 267–271 (1995).

A.S. Tse et al., *Macromolecules*, vol. 28, pp. 6533–6538 (1995).

S.A. Asher et al., *J. Am. Chem. Soc.*, vol. 116, pp. 4997–4998 (1994).

P. Bartlett et al., *Adv. Colloid Interface Sci.*, vol. 50, pp. 39–50 (1994).

McCurley, "An Optical Biosensor Using A Fluorescent Swelling Sensing Element", *Biosensors and Bioelectronics*, vol. 9, pp. 527–533 (1994).

S. Dosho et al., "Recent Study of Polymer Latex Dispersions", *Langmuir*, vol. 9, No. 2, pp. 394–411 (1993).

J. M. Peula et al., *Colloids Surf. A*, vol. 77, pp. 199–208 (1993).

C. Smits et al., *Adv. Colloid Interface Sci.*, vol. 42, pp. 33–40 (1992).

Sheppard, Jr. et al., "Design of a Conductimetric Microsensor Based on Reversibly Swelling Polymer Hydrogels", IEEE, pp. 773–776 (1991).

P.L. Flaugh et al., *Appl. Spectrosc.*, vol. 38, pp. 847–850 (1984).

P. Pieranski et al., *Phys. Rev. Let.*, vol. 50, pp. 900–903 (1983).

* cited by examiner

*Primary Examiner*—Mary E. Ceperley
(74) *Attorney, Agent, or Firm*—Baker Botts LLP

(57) ABSTRACT

Novel sensor devices composed of a crystalline colloidal array (CCA) polymerized in a hydrogel are disclosed. The hydrogels are characterized as being capable of shrinking and swelling in response to specific stimuli applied thereto. As the hydrogels shrink or swell, the lattice structure of the CCA embedded therein changes, thereby changing the wavelength of light diffracted by the CCA. Thus by monitoring the change in diffracted wavelength, the concentration of a stimulus is determined. The gels can be modified to sense numerous different stimuli. The sensor devices are specific in that they are modified to react with only one species or family of species. These sensors have various applications in areas including, for example, environmental and chemical systems, chemomechanical systems, sensor devices and medical diagnostic tools. Various methods for making and using these devices are also disclosed.

33 Claims, 9 Drawing Sheets

4 - acrylamidobenzo 18-Crown-6

N-isopropylacrylamide

Copolymer

POLYMERIZED CRYSTALLINE COLLOIDAL ARRAYS

CROSS-REFERENCE TO OTHER APPLICATIONS

This application is a continuation of U.S. application Ser. No. 08/819,240, filed Mar. 17, 1997, now U.S. Pat. No. 5,854,078 which is a continuation-in-part of U.S. application Ser. No. 08/743,816 filed Nov. 6, 1996, now U.S. Pat. No. 5,898,004.

This work was supported by Office of Naval Research Grant No. N00014-94-1-0592; the government has certain rights in this invention.

BACKGROUND OF THE INVENTION

1. Field of the Invention

The present invention generally relates to optical, gel-based devices that utilize the diffraction properties of crystalline colloidal arrays. More specifically, the present invention relates to polymerized crystalline colloidal array detectors whose diffraction wavelengths change in response to a variety of specific stimuli. These detectors have application in numerous chemical, environmental and medical technologies.

2. Background Art

Charged colloidal particles, when suspended in water, form a stable, crystalline dispersion due to interparticle coulomb repulsion forces. The property of structural ordering in such dispersions has been exploited in making devices such as narrow band optical rejection filters. The ordering phenomena in such colloidal suspensions have been useful in spectroscopy and Bragg diffraction techniques. It has been found that mesoscopic, crystalline structures can have many practical applications as optical filters in military, space, medical and research uses. In many such instances, it is necessary or desirable to filter narrow bands of selected wavelengths from a broader spectrum of incident radiation. Crystalline structures, or crystalline colloidal arrays (CCA), and their use in optical filtering devices are disclosed, for example, in U.S. Pat. Nos. 4,627,689 and 4,632,517.

Similar devices, in which a CCA is embedded in a polymer matrix, have also been disclosed. For example, U.S. Pat. Nos. 5,368,781 and 5,266,238 disclose tunable, narrow band radiation filters comprising a crystalline colloidal array of charged particles fixed in a hydrogel film. Methods for filtering incident radiation using these filters are also disclosed.

U.S. Pat. Nos. 5,330,685, 5,338,492 and 5,342,552 discuss narrow band radiation filters comprising a CCA of charged particles in a polymeric hydrogel. U.S. Pat. No. 5,281,370 also discloses a method of making a solid radiation filter material including one embodiment in which the particles in the array are fused together by polymerization.

Various sensor devices are also reported in the art. Schalkhammer, et al., disclose an optical sensor that utilizes the concept of pH-dependent swelling of special polymers. See Schalkhammer, et al., "The Use of Metal-island-coated pH Sensitive Swelling Polymers for Biosensor Applications", *Sensors and Actuators B*, Vol. 24–25, pp. 166–172 (1995). Conductimetric sensor devices have been proposed based on the selective swelling of hydrogels in response to pH by Sheppard, "Design of a Conductimetric Microsensor Based on Reversibly Swelling Polymer Hydrogels", *Transducers '91*, 773–776 (1991) and Sheppard, et al., "Microfabricated Conductimetric pH Sensor", *Sensors and Actuators B*, Vol. 28, pp. 95–102 (1995). Finally, sensor devices based on the selective swelling of hydrogels in response to glucose have been proposed by McCurley, "An Optical Biosensor Using A Fluorescent, Swelling Sensing Element", *Biosensors and Bioelectronics*, Vol. 9, pp. 527–533 (1994) and Kikuchi, et al., "Glucose-Sensing Electrode Coated With Polymer Complex Gel Containing Phenylboronic Acid", *Anal. Chem.*, Vol. 68, pp. 823–828 (1996).

None of the art, however, discloses a sensor device that utilizes crystalline colloidal array diffraction as a detection means, as disclosed herein.

SUMMARY OF THE INVENTION

The present invention is generally directed to devices comprising a hydrogel that undergoes a volume change in response to a specific chemical species, and a crystalline colloidal array (CCA) polymerized within said hydrogel. Because the volume of the hydrogel changes, the lattice spacing of the CCA embedded therein changes as well. The light diffraction properties of the CCA change as the lattice spacing is changed. Measuring the change in diffraction, therefore, indicates the presence or absence of the stimuli that causes the volume of the hydrogel to change. The present invention is also directed to methods for making and using these devices.

The devices of the present invention can be used to detect a number of specific stimuli. For example, they can be used to detect the presence of various chemicals, such as metal ions in solution and organic molecules such as glucose, making the devices useful for chemical analysis. The devices can also be used to detect the presence of various gasses in solution. As a biomedical detection device, these sensors can be used to detect the presence of antigens from various sources, antibodies from various sources, and viruses such as HIV. These devices can be further used as "sense and dispense" mechanisms which detect the presence of a particular stimulus and, in response to that stimulus, release a drug or other therapeutic agent. Since none of these devices is incompatible with living cells, their use both in vitro and in vivo is contemplated. One skilled in the art will appreciate that the various embodiments disclosed herein, as well as other embodiments within the scope of the invention, will have numerous applications in the environmental, medical, pharmaceutical, metallurgy and chemical fields.

It is an object of the present invention to provide a sensor device comprising a CCA polymerized in a hydrogel that changes volume in response to stimuli.

It is a further object of the invention to provide a sensor device that utilizes the light diffraction properties of a CCA to detect the presence of various stimuli.

A further object of the present invention is to provide a sensor device that swells in response to various stimuli, thereby changing the diffraction properties of the sensor.

Another object of the invention is to provide a sensor device for detecting the presence of chemicals.

Another object of the invention is to provide a sensor device for detecting the presence of gasses in solution.

Another object of the invention is to provide a sensor device for detecting the presence of various medical conditions.

Another object of the invention is to provide a sensor device for detecting the presence of biological molecules.

It is another object of the present invention is to provide a sensor device useful in environmental applications.

Another object of the present invention is to provide a sensor device having application in the field of medical diagnostics.

A further object of the present invention is to provide a sensor device useful for dispensing therapeutic agents in vivo in response to the presence of stimuli.

These and other objects of the invention will be more fully understood from the following description of the invention.

DESCRIPTION OF THE INVENTION

Figure 1:
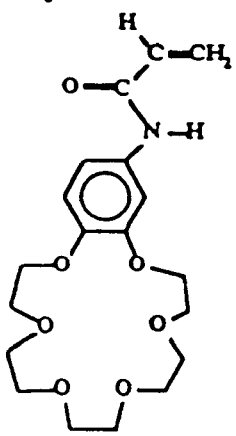
FIG. 1 is an illustration of the monomers used in a hydrogel according to one embodiment of the present invention.
Figure 1:
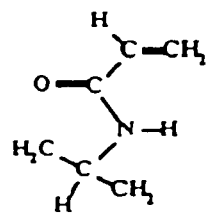
Figure 1:
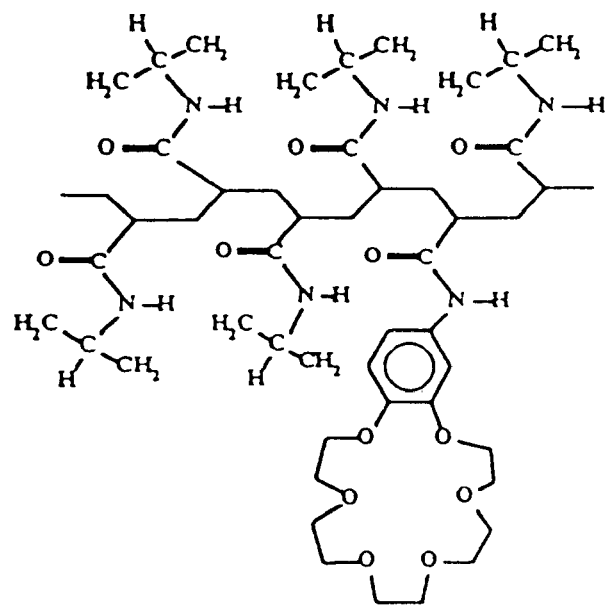

The sensor devices of the present invention generally comprise a hydrogel characterized by the property of undergoing a volume change in response to a specific chemical species; and a light diffracting crystalline colloidal array of charged particles polymerized in said hydrogel, said crystalline colloidal array having a lattice spacing that changes when said volume of said hydrogel changes thereby causing the light diffraction of said crystalline colloidal array to change. Thus, these devices are optical, gel based sensors that combine the light diffraction properties of crystalline colloidal arrays (CCA) with the conformational changes that various polymers undergo in response to external stimuli.

Monodisperse, highly charged colloidal particles dispersed in very low ionic strength liquid media self-assemble due to electrostatic repulsion to form CCA. These ordered structures are either body-centered cubic (BCC) or face-centered cubic (FCC) arrays with lattice constants in the mesoscale range (50–500 nanometers (nm)). Just as atomic crystals diffract x-rays meeting the Bragg condition, CCA diffract ultraviolet (UV), visible and near infrared (IR) light. CCA can be prepared as macroscopically ordered arrays from non-close packed spheres. Such arrays exhibit highly efficient Bragg diffraction; nearly all light meeting the Bragg condition is diffracted, while adjacent spectral regions not meeting the Bragg conditions will freely transmit. "Non-close packed spheres" refers to an ordering wherein the spheres are spaced by some distance from each other. The Bragg diffraction law is represented by the following formula:

$$m \lambda = 2 \, nd \sin \theta$$

where m is the order of diffraction, $\lambda$ is the wavelength of incident light, n is the suspension refractive index, d is the interplanar spacing, and $\theta$ is the angle between the incident light and the crystal planes.

Some polymers reversibly change conformation in response to a specific external stimulus. For example, almost all polymers undergo some reversible conformational change with changes in solvents, and some, such as poly N-isopropylacrylamide, undergo conformational changes in response to temperature changes. Solutes that interact with the side groups on the polymer backbone may also induce conformational changes; introduction of ionized groups onto the backbone of the polymer thus sensitizes the polymer conformation to changes in ionic strength. Polymers that change conformation in response to the concentration of a single, specific solute can therefore be prepared by adding to that polymer a functional group that selectively interacts with that single solute. Such polymers can be further mixed with crosslinking agents to form gels that exhibit the same response to stimuli as the polymer from which they are formed. For example, these gels will undergo volume changes at conditions when the constituent polymer chains change conformation. Volume changes between 0.1 and 50%, or even greater, are contemplated by the present invention. The volume response exhibited by these hydrogels allows for their broad application in areas including but not limited to chemomechanical systems, separation devices and sensor devices.

The present invention is directed to a sensor device comprising: a hydrogel characterized by the property of undergoing a volume change in response to a specific chemical species; and a light diffracting crystalline colloidal array of charged particles polymerized in said hydrogel; said crystalline colloidal array having a lattice spacing that changes when said volume of said hydrogel changes, thereby causing the light diffraction of the crystalline colloidal array to change. The hydrogel in one embodiment of the present invention generally comprises a crosslinking agent, a gel component and a molecular recognition component. The crosslinking agent can be any crosslinking agent compatible with the other components of the hydrogel. Examples of suitable crosslinkers include N,N'-methylenebisacrylamide, methylenebismethacrylamide and ethyleneglycol-dimethacrylate, with N,N' methylenebisacrylamide being preferred. In addition to forming the polymer network in the CCA, the cross-linking agent as used in this step assists formation of the hydrogel and strengthens the resulting hydrogel film so that a self-supporting film results. Hydrogel films can be formed when as little as 1 part in 100 parts by weight of the monomer mixture is the cross-linking agent. Generally, increasing the amount of crosslinking agent lowers the sensitivity of the gel to the analyte being detected. Preferably, crosslinker is used in an amount between about 4 and 15% of monomer weight, more preferably about 5% of monomer weight.

The gel monomer component of the hydrogels of the present invention can be any compound that forms a hydrogel that undergoes a volume change in response to a stimulus or stimuli. Examples of suitable gels include, but are not limited to, acrylamide gels, purified agarose gels, N-vinylpyrolidone gels and methacrylate gels. Preferred gels for use in the present invention are N-isopropylacrylamide (NIPA) and acrylamide.

The phase transition properties of the hydrogel are modified by functionalizing the hydrogel with a reagent that specifically binds an analyte of interest. Thus the gel is modified so as to detect the presence of a stimulus by means of this molecular recognition component. More specifically, a monomer capable of selectively interacting with a specific solute is incorporated in the hydrogel. Typically, the more of the molecular recognition component, the more sensitive the device to the desired analyte. This relationship, however, is only observed up to a certain concentration of the molecular recognition component, after which the sensitivity of the gel decreases. Any monomer having molecular recognition capabilities for the desired solute can be used. For example, 4-acrylamidobenzo 18-crown-6 ether, which selectively binds Group I cations and preferably binds potassium ions, can be used if potassium is the analyte of interest. Other crown ethers, cyclodextrans, caloxarenes, and other chelating agents can also be used.

When the analyte binds to the gel matrix, it causes a change in the hydrophilicity of the matrix, and therefore changes the swelling properties of the gel. As the hydrogel shrinks and swells, the CCA embedded in the hydrogel follows. As the CCA changes dimension, the resulting diffraction wavelength alteration reports on the array volume change. The diffraction shifts to shorter wavelengths as the gel shrinks, and to longer wavelengths as the gel swells. Measuring this alteration, therefore, allows for detection of the stimulus which caused the volume change.

In addition, a third monomer component can be added to change the sensitivity of the device by making the hydrogel even more hydrophobic or hydrophilic, as desired by the needs of the user. The more hydrophobic the gel, the more it tends to stay in a collapsed or shrunken state. For example, an acrylamide, which is more hydrophilic than NIPA, can be added, or N-butylacrylamide, which is more hydrophobic than NIPA, can be added to adjust the properties of the hydrogel.

As stated above, the devices of the present invention combine CCA technology with modified hydrogels to provide devices useful, for example, as sensor devices. More specifically, a hydrogel having the characteristics described above is polymerized around a fluid CCA. Changes in the volume of the hydrogel matrix change the lattice spacing of the embedded CCA, thus changing the color of the light diffracted. These devices are well suited for sensor applications due to the unique ability to directly measure the volume change of the hydrogel by monitoring the diffraction wavelength from the CCA. In many applications, the change in color can be detected by the unaided eye. For example, less than a 5% expansion in volume can yield a color change detectable by the unaided eye.

A method for making a device according to the present invention generally comprises the steps of allowing charged particles to self assemble into a crystalline colloidal array; adding a first comonomer that is a gel monomer, a crosslinking agent, a second comonomer that is a molecular recognition monomer to a medium comprising said crystalline colloidal array and a polymerization initiator; and polymerizing the mixture to form a crystalline colloidal array embedded in a hydrogel.

An alternative method for making a device according to the present invention generally comprises the steps of allowing charged particles to self assemble into a crystalline colloidal array; adding a crosslinking agent, a gel monomer, and a polymerization initiator; polymerizing the mixture to form a crystalline colloidal array embedded in a hydrogel; and adding a molecular recognition component capable of binding with the hydrogel.

Any suitable particles can be used. For example, the particles used to create the CCA can be colloidal polystyrene, polymethylmethacrylate, silicon dioxide, aluminum oxide, polytetrafluoroethylene or any other suitable materials which are generally uniform in size and surface charge. Colloidal polystyrene is preferred. The particles are chosen depending upon the optimum degree of ordering and the resulting lattice spacing desired for the particular application. The particles preferably have a diameter between about 50 and 500 nanometers and may be either synthesized as discussed below or obtained commercially. Electrically charged particles that can be used in accordance with this embodiment are commercially available from Dow Chemical or Polysciences, Inc.

Monodisperse particle colloids can be prepared by emulsion polymerization or any other means. For example, an emulsion polymer colloid can be prepared by mixing the desired monomer with a cross-linking agent, a surfactant to aid in the formation of the emulsion, a buffer to keep the pH of the solution constant and to prevent particle coagulation, and a free-radical initiator to initiate polymerization. In a preferred embodiment, the monomer is styrene, the crosslinking agent is divinylbenzene, the surfactant is sodium-di(1,3-dimethylbutyl)sulfosuccinate, the initiator is preferably potassium persulfate and an ionic comonomer is also added, preferably 1-sodium, 1-allyloxy-2-hydroxypropane sulfonate. Other suitable compounds can also be used to prepare the emulsion polymer colloid, so long as compatibility problems do not arise. The particles should then be purified by the use of centrifugation, dialysis and/or an ion exchange resin. Purification of the commercially available particles is also required.

Following polymerization, the particles may be stored in an ion exchange resin, preferably in a bath of 10% by weight suspension of ion exchange resin such as analytical grade AG51X8 mixed bed resin commercially available from Bio-rad of Richmond, California. The ion exchange resin should preferably be cleaned prior to use through a suitable procedure such as that of Vanderhoff et al. in the *Journal of Colloid and Interface Science*, Vol. 28, pp. 336–337 (1968).

The electrically charged particles are then allowed to self assemble to form a crystalline colloidal array. This assembly takes place in a suitable solvent, preferably water. To the CCA medium is then added a gel monomer, a molecular recognition monomer, a cross-linking agent and a polymerization initiator. Any suitable initiator can be used, such as a thermal initiator or a photoinitiator. Preferably, a UV photoinitiator is used. A preferred UV photoinitiator for this use is 2,2'-diethoxyacetophenone. Any cross-linking agent, gel monomer and molecular recognition monomer discussed above can be used.

After formation, the mixture is then polymerized. Any means known in the art can be used to initiate polymerization, so long as the method for polymerization does not destroy or otherwise disorder the CCA. Preferably, the polymerization is accomplished by placing the mixture between two plates, preferably quartz plates separated by a parafilm spacer, at a temperature from between about 0° to 10° C. The plates are then exposed to UV light. Exposure to the UV light effects complete polymerization after about 5 minutes. Upon completion of the polymerization, the plates are removed and a stable polymerized CCA (PCCA) results. This film can be approximately about 150 microns thick and can be made thinner based upon the needs of the user.

In a preferred embodiment, the hydrogel is composed of a copolymer of NIPA and 4-acrylamidobenzo 18-crown-6 ether crosslinked with N,N'-methylenebisacrylamide. This embodiment is depicted in FIG. 1. The crown ether in the hydrogel complexes with metal cations, with an affinity that depends both on the ability of the cation to fit into the cavity of the crown ether, and the charge of the ion. The NIPA gel is moderately hydrophilic. The copolymer is highly sensitive to slight changes in its hydrophilicity due the complexation of small amounts of cations. As the crown ether binds with cations, the entire copolymer becomes more hydrophilic causing the PCCA to swell and the diffraction wavelength to increase. The linear NIPA/crown ether copolymer is only moderately hydrophilic and precipitates out of solution above about 38° C. At 23° C., however, the polymer-solvent attraction is only slightly greater than the polymer-polymer attraction in the hydrogel.

The device of the preferred embodiment is particularly useful as a sensor for lead. The detector swells in lead concentrations between about 2 $\mu$M and about 10 mM. This detector functions as an easy to use, sensitive detector which is blue at lead concentrations of about 2 $\mu$M or less and green at concentrations of about 20 $\mu$M. The color change of the device can be detected by the unaided human eye at lead concentrations of approximately 15 $\mu$M, and can be detected by spectrophotometry at even lower concentrations. At concentrations higher than about 20 mM, the device shrinks and the wavelength diffracted gets smaller. The sensor is reversible and the diffraction reverts to its original wavelength when the lead is allowed to exchange out. For example, the PCCA completely returns to about its original volume and diffraction wavelength after soaking for a few minutes in deionized water. Diffraction peak maxima of the PCCA are reproducible to within 1 nm after successive washings and reimmersion in lead solutions, at a constant temperature of 23° C. Similar lead sensors can be fabricated using acrylamides that do not have a volume temperature dependence.

In addition, the device of the preferred embodiment also selectively binds group I cations, preferably binding potassium over sodium. The PCCA swells in potassium chloride (KCl) solutions at concentrations ranging from 1 to 20 mM at 23° C. and the gel begins to contract at higher KCl concentrations. Sodium ions, which have a lower affinity for the crown ether group, have little effect on the diffraction below approximately 20 mM. The maximum diffraction wavelength shift from pure water to 100 mM sodium ions is only about 15 nm whereas the maximum diffraction wavelength shift from pure water to 20 mM potassium ions is about 100 nm. The device is sensitive to concentrations of potassium ions less than 1 mM; the diffraction wavelength of the PCCA shifts 25 nm between the pure water and 1 mM KCl, which shift can be seen by the unaided human eye. Thus, the device functions as a sensitive and easy to use detector for potassium as well as lead, with a 500 fold greater affinity for lead than potassium.

Alternatively, the incorporation of other crown ethers in the hydrogel could produce a sensor that selects other cations. The selectivity of the sensor is limited by non-selective binding of the crown ether with other cations. Similarly, use of functionalized compounds other than crown ethers, such as cyclodextrans, caloxarenes or other chelating agents, can produce devices that respond to still other stimuli.

The response rate of the PCCA described above as the preferred embodiment, having a thickness of about 150 microns, is typically less than about 5 minutes. Response rate can be improved by decreasing the thickness of the PCCA. The response rate is partially determined by the mass transport of cations into the gel, and partially determined by the kinetics of complexation. Decreasing the gel thickness and the monomer content of the gel will markedly increase the rate of analyte mass transport to the active sites on the gel, and therefore decrease response time. Response rate will also be effected by the molecular recognition component used, as some will be more selective than others. Response rates of between about 1 and 5 minutes can be achieved with a 150 micrometer thick gel and response rates on the order of seconds can be achieved with thinner gels. The response rate is inversely proportional to the thickness of the gel.

In addition, the present invention contemplates embodiments in which the gel monomer will change volume in response to temperature changes. For example, NIPA hydrogels change volume with changes in temperature. Temperature has a large effect on the diffraction of the sensor in a particular concentration of KCl. The diffraction wavelength of the sensor in 5 mM KCl is 595 nm at 23° C., but increases to 710 nm at 7° C., and decreases to 495 nm at 32° C. Thus, if using a hydrogel that is also responsive to temperature, the sensor should be maintained at a constant temperature during use.

In another embodiment of the present invention, the hydrogel in which the CCA is polymerized comprises a crosslinking agent, a gel monomer and a biomolecular recognition component. This biomolecular recognition component is a biomolecule that selectively binds a specific chemical specie as part of its biological function. This component can be bound to the gel directly or by one or more linking molecules. Examples of such biomolecular recognition components include but are not limited to enzymes, antibodies, antigens, porphyrins, ferritin, or pheromone receptors. These natural recognition components can respond to simple chemical species, or to the presence of particular proteins. These sensor devices can therefore further comprise one or more linking molecules that bind the biomolecular recognition component to the gel monomer. In addition, the biomolecular recognition component can be modified by being reacted with a molecule that can be bound to the linking agent, or to the gel itself. A particularly preferred linking molecule is 5-(biotinamido)pentylamine, and a preferred molecule for reaction with the biomolecular recognition component is avidin; avidin is a protein extracted from egg whites and has four binding sites for biotin. The sensor devices of this embodiment have particular application in the area of detection of disease markers, for example in detecting the presence of HIV antibodies. The gel can be sensitive to very low concentrations of species, if the recognition element has a high binding constant. This is attributable to the fact that the PCCA recognition element concentrates the analyte within the PCCA.

For example, an antigen can be added to a gel monomer to form a hydrogel that binds such things as antibodies to tuberculosis cells, cancer cells, or HIV. The antigen is chosen based on what medical condition is to be detected. Enzymes can also be attached to the gel for medical diagnostics. For example, binding glucose oxidase to the hydrogel will allow for the detection of glucose. Thus this embodiment of the present invention has application as a medical diagnostic tool. As above, the sensitivity of the sensor can be adjusted to the desired concentration by modifying the ratio of gel monomer to recognition component, the degree of crosslinking and the hydrophobicity of the gel monomer. Hydrophobicity can be adjusted as discussed above with the addition of another monomer that is either more or less hydrophobic than the gel monomer, depending on the needs of the user.

These biomedical sensors have potential applications both in vitro and in vivo. When used in vivo, these devices can use a "sense and dispense" mechanisms, first by sensing or detecting the presence of a chemical, or other indicia of a medical condition, and then by releasing a therapeutic agent in response to the chemical. More specifically, the hydrogel would bind to a particular stimulus that would cause the gel to swell. This swelling would allow for release of a therapeutic agent trapped within the device when the gel is in a shrunken state.

The antibody and antigen based sensors function much the same way as the chemical sensors discussed above. That is, the gel volume changes when the gel becomes bound to a chemical specie that changes the hydrophobicity of the gel.

In the case of the enzyme based sensors, the enzyme changes the chemical nature of the analyte by first binding to the analyte substrate and then cleaving or otherwise reacting with the analyte substrate. The gel of the enzyme based sensors swells because the interior of the gel has a high concentration of reaction products and a low concentration of analyte substrate, while the liquid surrounding the gel has the opposite characteristics. This causes an osmotic pressure imbalance between the inside and outside of the gel. A solvent, preferably water, diffuses into the gel to relieve that pressure imbalance; it is this excess solvent that causes the gel to swell. If immersed in a fresh solution of the substrate, the sensor will expand again. The response of the sensor, therefore, is dependent upon the concentration and amount of substrate in its immediate environment.

The biomedical devices are made by polymerizing a CCA in a hydrogel comprising a crosslinking agent and a gel monomer such as those described above. Following formation of the PCCA, a molecular recognition component is added. In the preferred embodiment, addition of the molecular recognition component is accomplished by first hydrolyzing the PCCA. Any means known in the art can be used to effect hydrolysis; a preferred method is to place the PCCA in a 0.1 M solution of sodium hydroxide for about 10 minutes. Hydrolysis of the PCCA serves to establish acidic, reactive sites on the PCCA matrix. Preferably, the hydrolysis is a partial hydrolysis in which 10 to 30% of the reactive sites on the PCCA matrix have been acidified. This is accomplished by hydrolyzing for about 10 minutes. The acidified PCCA is then reacted with a linking molecule and a coupling agent that binds the compound in place of the acid groups on the matrix. A preferred linking molecule is a 5-(biotinamido)pentylamine and a preferred coupling agent is 1-(3-dimethylaminopropyl)-3-ethylcarbodiimide. Other compounds and water soluble coupling agents can also be used. As will be appreciated by one skilled in the art, the reaction can be performed without a coupling agent, but would proceed more slowly if one is not used. The PCCA should be reacted with the linking molecule for a period of time sufficient to effect reaction of all of the acid; when using a coupling agent this is typically between about 3 to 6 hours. A molecular recognition component, such as an enzyme, antibody or antigen, is then added, and binds to the compound. The molecular recognition component is first bound to a compound having an affinity for the linking molecule. A preferred compound for this use is avidin, which is preferred when using biotin as the linking molecule. Thus the enzyme is bound to the PCCA without destroying the CCA structure or the reactivity of the enzyme. In principle, any biomolecule that can be avidinated can be incorporated onto the PCCA according to this embodiment of the present invention. For example, recognition elements such as antigens that bind HIV antibodies can be attached to the PCCA to create clinical diagnostic sensors. The sensitivity and useful dynamic range of the PCCA sensors can be simply adjusted by changing the gel monomer-recognition element concentration ratio, as well as altering the degree of hydrogel crosslinking.

The enzymes bound to the PCCA then react with a specific compound. For example, if glucose oxidase is used as the enzyme, the gel will cleave glucose, and if β-D-galactosidase is used as the enzyme the gel will cleave β-D-galactose. Reaction of the sensors with the specific compound causes the PCCA diffracted wavelenth to shift. For example, exposure of a glucose oxidase labelled PCCA to glucose causes the hydrogel to swell, which shifts the PCCA diffracted wavelength towards the red end of the spectrum. The glucose sensor PCCA swells in glucose concentrations of between about 0.1 mM and 0.5 mM solutions. The sensor swelling saturates above about 2 mM glucose due to formation of a steady state for the glucose oxidase conversion of glucose to gluconic acid and for the reoxidation of the enzyme by dissolved oxygen. The glucose sensor returns to its original volume and diffraction wavelenth after removal from the glucose solution. The glucose oxidase enzyme remains biologically active for at least about four months.

The swelling of the enzyme sensor appears to be due to formation of an anionic reduced flavin in the glucose oxidase enzyme upon glucose turnover, although the inventors do not wish to be bound by this mechanism. The oxidized form of the enzyme is uncharged at neutral pH. The reduced flavin prosthetic group, however, is anionic at neutral pH. The resulting electrostatic repulsion between reduced flavin moieties causes the gel to swell. The reduced form of the enzyme is reoxidized by $O_2$ in the solution:

$$E + \text{Glucose} \rightarrow EH_2^{1-} + \text{Gluconic Acid } EH_2^{1-} + O_2 \rightarrow H_2O_2 + E$$

The electrostatic nature of the gel swelling can be confirmed by addition of salts such as NaCl in a concentration of about 0.2 mM, which screen the electrostatic interactions.

As will be appreciated by those skilled in the art, the biomolecular recognition component can be added in numerous ways. In the preferred embodiment described above, this addition is effected by reacting the biomolecular recognition component with avidin, which binds to the 5-(biotinamido)pentylamino bound to the gel matrix. This method, therefore, essentially uses two linking molecules. Embodiments using only one linking molecule or more than two linking molecule, or use of no linking molecule at all, are also within the scope of the invention.

One application of the devices of the present invention is as an implant that would be placed directly under the skin. The device would detect a specific chemical stimulus in the body and undergo a volume change in response thereto. As a result of the volume change, the lattice structure of the CCA, and therefore the diffracted wavelength of the CCA, would also change. This color change could be detected through the skin. Alternatively, a device diffracted in the infrared range could be placed more deeply under the skin, such that the color change would not be visible unless an IR light source and a spectrometer was used.

Another application for the devices of the present invention is to determine the concentration of a particular analyte as present in tear fluid. In this embodiment, the device would be similar to a contact lens, but would contain a sensor for determining the concentration of various analytes in the tear fluid, for example the glucose level in the tear fluid. The device would change color as the analyte concentration changed. Such devices are preferably incorporated at or near the rim of the lens, so as not to interfere with the vision of the user.

In another embodiment of the present invention, the PCCA gels as discussed above are used to fabricate novel optrode sensors. In this embodiment, the PCCA is attached to the end of a fiber optic; light channelled down the fiber will be diffracted back into the fiber to carry information on the PCCA volume, and thus the analyte concentration. This embodiment is very sensitive, since a spectrometer can be used to detect very small changes in diffracted wavelength. In addition, a very fast response speed is observed. Such an optrode can be easily miniaturized since only a small piece, approximately 1 $\mu m^3$ or smaller, of the PCCA is needed for the sensor.

For example, a small optrode, such as one that is as small as a few microns in thickness, can be inserted into small analyte solution volumes, into small pieces of tissue, or into a living person for clinical chemical measurements. The sensor could be modified to detect for various stimuli, such as salts, hormones, nucleic acids, amino acids, proteins or other biological species in areas as small as a single cell. In addition, by attaching a plurality of these optrode fibers and sensor arrays for different species along the slit of a spectrograph attached to a CCD camera, hundreds of different analyte concentrations can be simultaneously determined through the parallel detection of the diffracted wavelengths from these plurality of optrodes. Each of the optrodes could be attached to a different sensor with each sensor detecting a different specie, or a different concentration range of a specific specie. These optrode fibers could be designed to work by channelling light down the fiber, which will be diffracted back to a spectrometer to carry information on the PCCA volume.

In yet another embodiment of the present invention, interpenetrating networks (IPNs) can be used to produce sensors with recognition elements that are normally incompatible with the required self assembly of the CCA prior to polymerization into a PCCA. For example, some molecular recognition functionalized comonomers may be ionic, and would screen the electrostatic colloidal particle repulsive interactions required for CCA self assembly. In this case, the sensor is made in two steps.

First, a loosely crosslinked PCCA is formed without the molecular recognition element. Following formation of this PCCA, the functionalized monomer having the recognition element is diffused into the existing PCCA network. A second polymerization is then effected, wherein the polymer chains of the second network will form an interpenetrating network within the voids of the first network. The second network of the IPN will shrink or swell in response to the presence of the analyte, and the PCCA will expand or contract along with the second network due to the physical entanglement of the two networks.

Methods of using the above devices for detecting the concentration of a selected chemical specie are also provided. Following polymerization of the CCA in the hydrogel, these methods of use further include the steps of measuring the diffracted wavelength of said crystalline colloidal array polymerized in said hydrogel; contacting said polymerized crystalline colloidal array with said solution; measuring the diffracted wavelength of said crystalline colloidal array following exposure to said solution; and comparing the change in diffracted wavelength to determine concentration of said chemical specie. As discussed above, when a stimulus, such as a chemical specie, becomes bound to said hydrogel thereby causing the volume of the hydrogel to change, the lattice spacing of the CCA also changes. Accordingly, the diffracted wavelength of the CCA changes as the volume of the hydrogel changes. By determining the change in diffracted wavelength, the volume change of the hydrogel, and therefore the concentration of the chemical specie, can be determined. The higher the concentration of the chemical specie, the greater the swelling volume of the gel.

The change in diffracted wavelength can be determined by using instrumentation, such as a spectrometer or a spectrophotometer. In many cases, the diffracted wavelength change can also be seen by the unassisted human eye because the device will change color.

The present invention is also directed to sensors that do not utilize electrostatic interactions for volume changes, but instead utilize the non-ionic volume phase transition phenomenology of NIPA-like hydrogels. The volume phase transition temperature would shift as analytes bound to the recognition elements and the volume would change to alter the diffracted wavelength.

EXAMPLES

The following examples are intended to illustrate the invention and should not be construed as limiting the invention in any way.

Example 1

Charged polystyrene particles were formed by placing approximately 50 g of polystyrene and about 4 g of 1-sodium, 1-allyloxy-2-hydroxypropane sulfonate into about 100 g of water. About 4 g of sodium-di(1,3-dimethylbutyl)sulfosuccinate, about 0.1 g of buffer and about 0.5 g of sodium persulfate dissolved in about 3 ml of water were also added. The mixture was reacted for about 3.5 hours in a flask equipped with a stirring mechanism set at about 355 rpm. The particles were about 105 nm in diameter and were purified by dialysis and ion exchange.

A portion of the colloid suspension was removed and further dialysized for about one week in deionized water. The solution was then diluted about three-fold, and further purified by shaking with ion exchange resin until all of the impurity ions were removed and the CCA self assembled.

A PCCA was then made by adding to 3 ml of the CCA medium to a mixture comprised of about 0.15 g NIPA, about 0.07 g of 4-acrylamidobenzo 18-crown-6 ether, about 0.014 g of N,N'-methylenebisacrylamide and about 0.01 g of diethoxyacetophenone. The CCA was allowed to self assemble and the CCA/gel mixture was placed between two quartz plates. The plates were then exposed to UV light for about 5 minutes. The temperature was maintained at about 5° C. throughout.

Example 2

Figure 2:
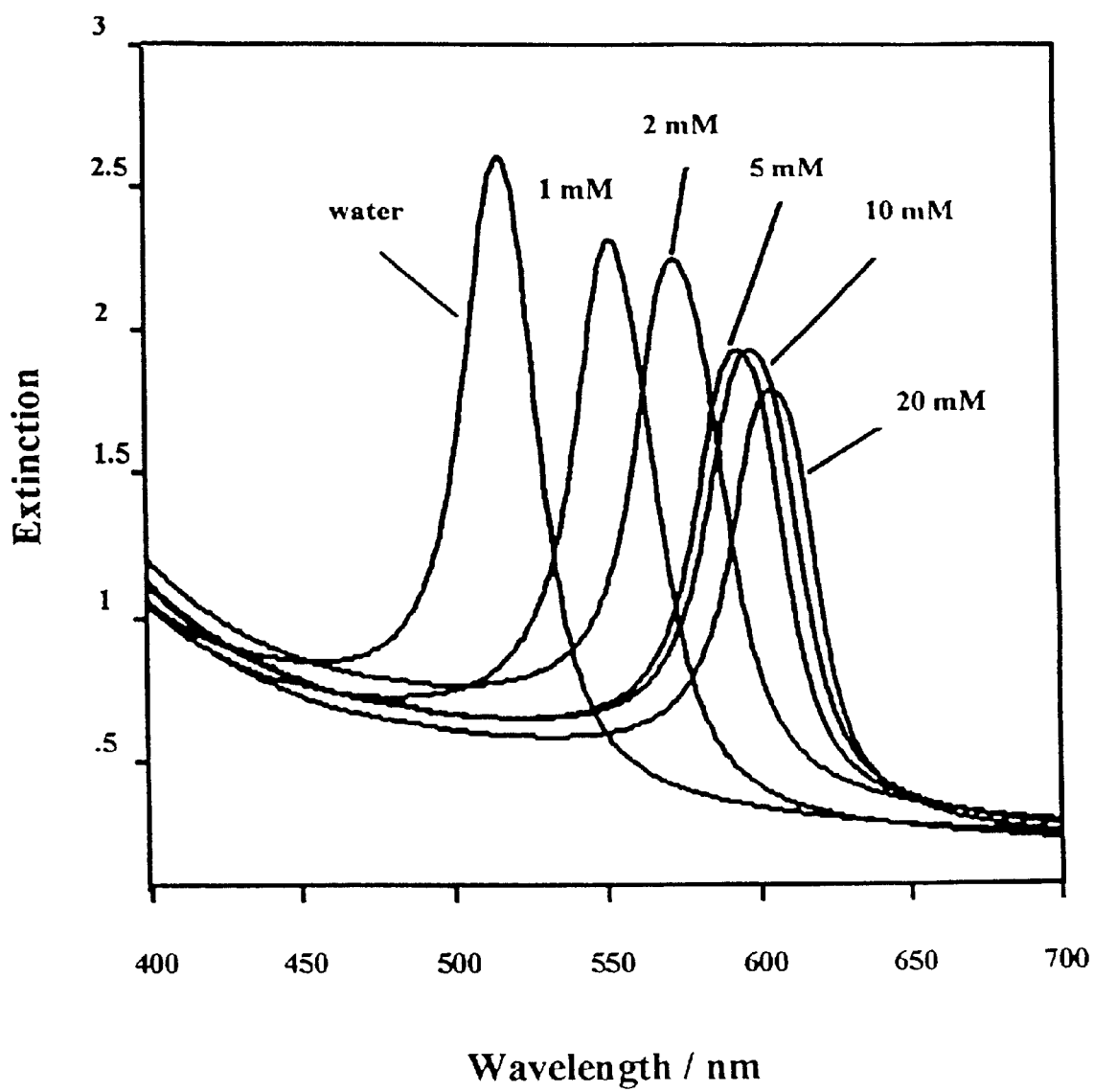
FIG. 2 demonstrates the diffraction wavelength dependence of a sensor device of the present invention on KCl concentration, as determined by the methods of Example 2.
Figure 3:
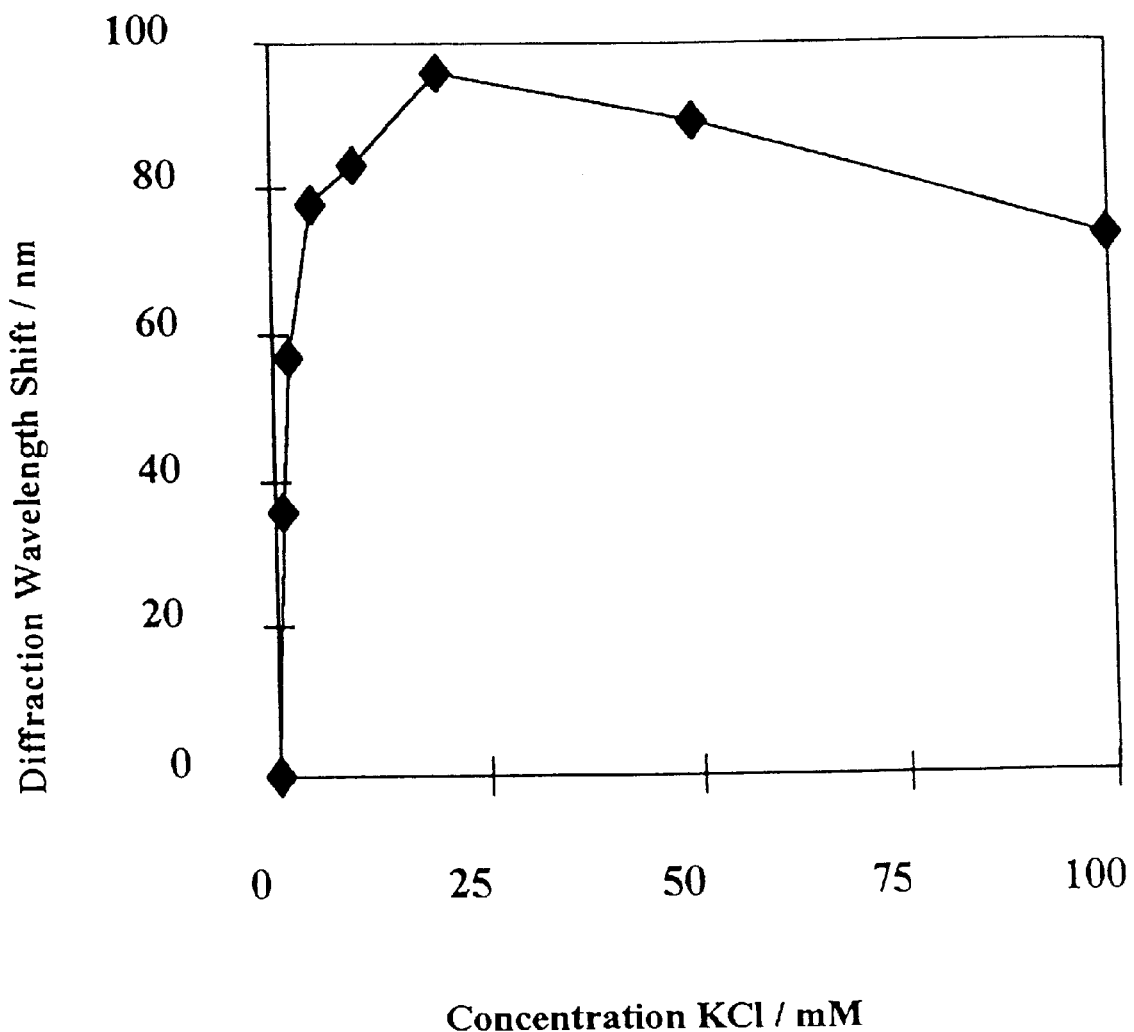
FIG. 3 illustrates the response of a PCCA in KCl concentrations ranging between 0 and 100 mM as determined by the methods of Example 2.

The PCCA sensor made according to Example 1 was tested in potassium chloride (KCl) concentrations ranging from 1 mM to 20 mM at 23° C. As the crown ether complexed potassium cations, the gel volume increased. The response to KCl was non-linear as can be seen from the extinction spectra of the PCCA sensor in KCl solutions of varying concentration, as is illustrated in FIG. 2. At KCl concentrations above 20 mM, the PCCA began to shrink, as is shown in FIG. 3. The sensor returned to its original diffraction color when removed from the KCl solution and immersed in a deionized water bath for 30 minutes. The response was also found to be reproducible; the diffraction peak centers of the PCCA in 5 mM KCl differed by no more than 1 nm after successive washings and re-immersion in 5 mM KCl at a constant temperature of 23° C.

Example 3

Figure 4:
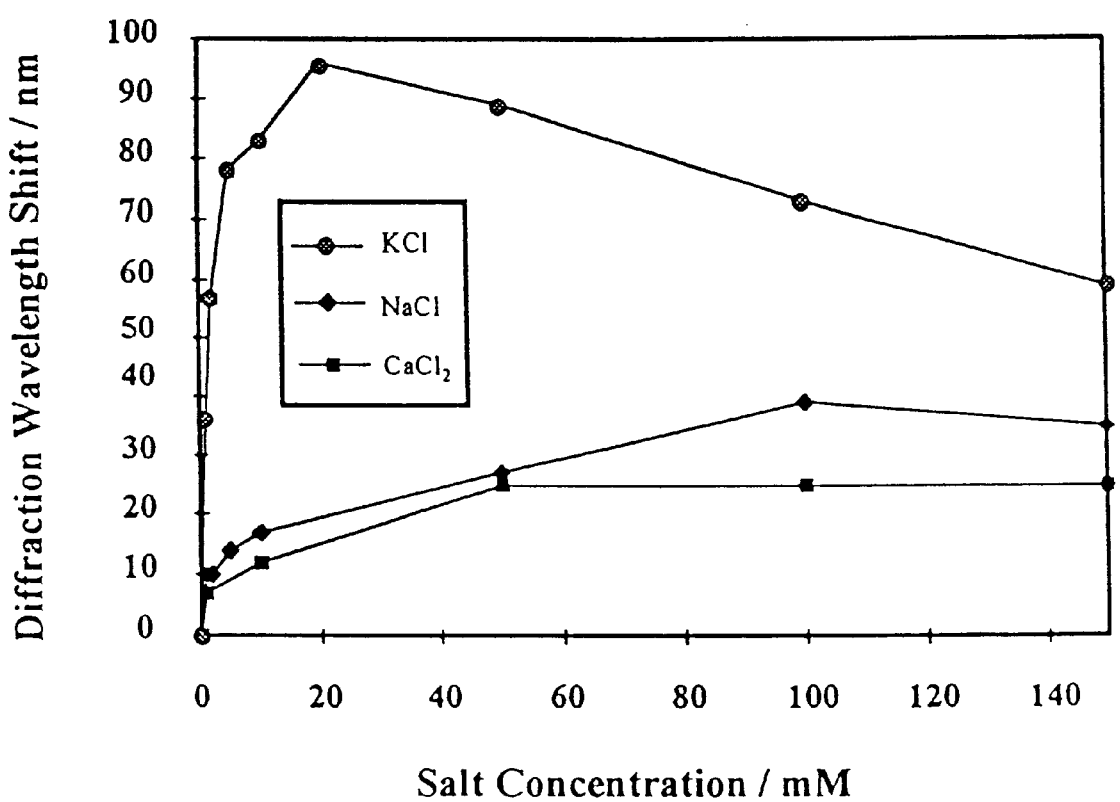
FIG. 4 shows diffraction wavelength shifts of one embodiment of the present invention in response to various cations, as determined according to the methods of Example 3.

The affinity of the PCCA described in Example 1 for both potassium and sodium was studied. Although the binding constants of 18-crown-6 type cyclic ethers are highest for potassium, these crown ethers still complex other cations. The maximum diffraction wavelength shift of the sensor in the presence of NaCl was 27 nm, which occurred at 100 mM NaCl. The sensitivity to NaCl is significantly lower than the response to KCl, which induced a 100 nm shift at 20 mM KCl. Calcium, although slightly smaller than sodium, caused a diffraction wavelength red shift of only 25 nm at 200 mM. The maximum response of the sensor to NaCl and $CaCl_2$ occurred at much higher concentrations than the maximum response to KCl. The diffraction wavelength shift of the sensor in KCl, NaCl and $CaCl_2$ solutions is depicted in FIG. 4.

This example illustrated that sodium ions do compete with potassium ions for crown ether binding sites. In 5 mM of KCl, the diffraction wavelength shifted by 90 nm from the diffraction wavelength in pure water. When immersed in a solution of 5 mM NaCl and 5 mM KCl (10 mM total salt), the diffraction wavelength shifted from the value in water by 75 nm. When the 5 mM KCl solution also contained 100 mM NaCl, the diffraction shift was only 55 nm. The diffraction wavelength in the 100 mM NaCl/5 mM KCl solution indicates a KCl concentration of approximately 1.3 mM, based on the calibration curve shown in FIG. 4.

Example 4

Figure 5:
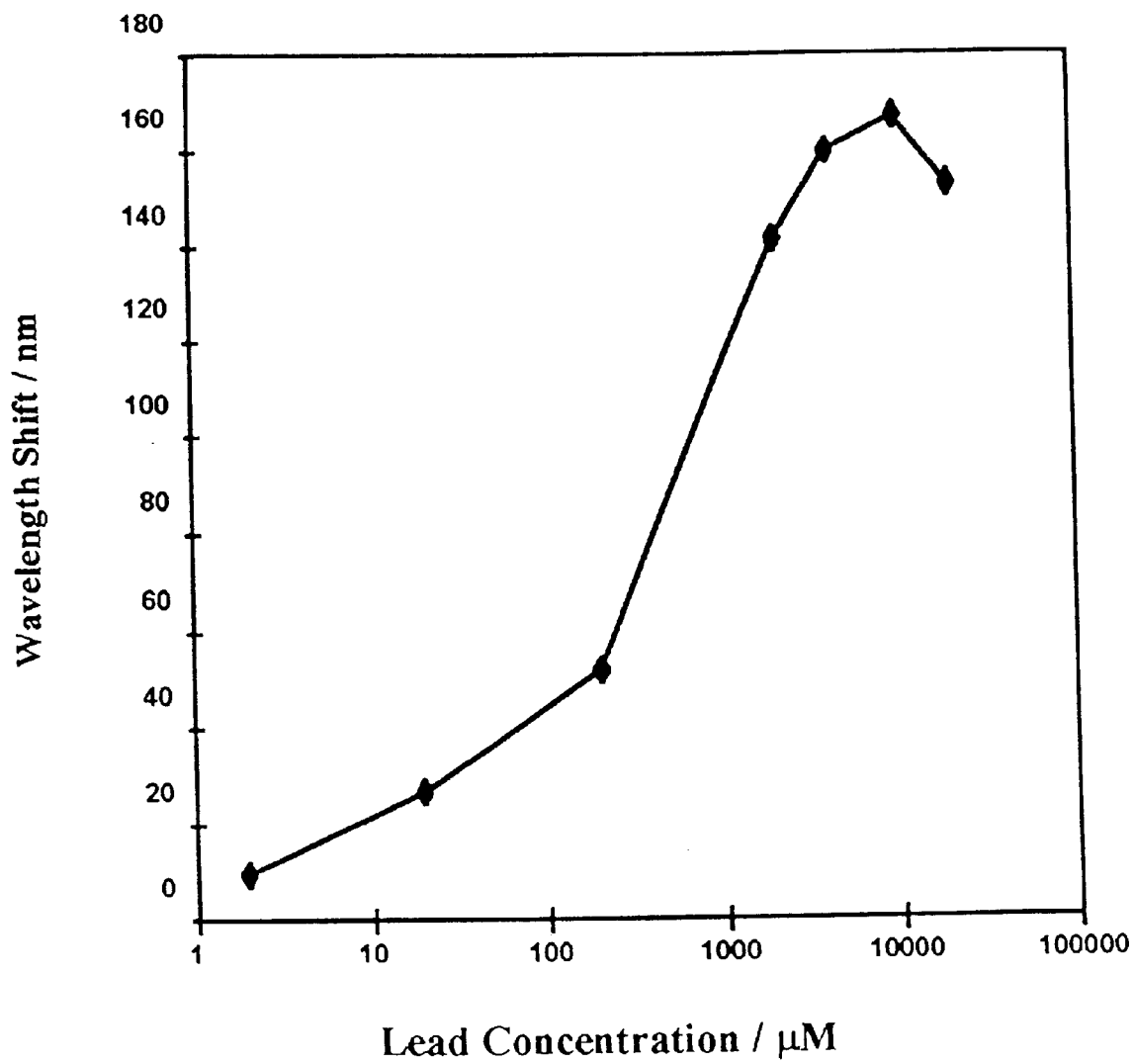
FIG. 5 shows the diffraction of a PCCA in response to various lead concentrations, as discussed in Example 4.

The response of the PCCA described in Example 1 to very low concentrations of lead II acetate was determined. The sensor had a response, detectable in the spectrometer, of a 10 nm shift in response to a 2 $\mu$M (approximately 410 ppb) concentration of lead II acetate. The response of 28 nm to 20 $\mu$M (about 4.1 ppm) lead II acetate is easily detectable with the unaided human eye. The device is blue at lead concentrations of 2 $\mu$M and green at lead concentrations of 20 $\mu$M. The lead response reached a maximum between 10 and 20 mM; the diffraction in 20 mM lead acetate is at a lower wavelength than the diffraction in 10 mM of lead to acetate. The shift in the PCCAs diffraction due the entire detectable concentration range of lead is shown in FIG. 5. The sensor returned to its original diffraction color when removed from the lead II acetate solution and immersed in a deionized water bath for 30 minutes. Due to the electrostatic character of the crown ether and cation interaction, this PCCA was found to be about 500 times more effective as a sensor for lead ions than for potassium ions. This device, therefore, functions as a lead detector.

Example 5

A sensing device was made by taking a blue diffracting suspension of polystyrene colloids prepared as described above in Example 1 and polymerizing a CCA of these colloids in an acrylamide gel. The PCCA was then immersed in a 0.1 M sodium hydroxide bath for about 10 minutes, which hydrolyzed some, but not all, of the $CONH_2$ groups to COOH. The hydrolyzed gel was washed in pure water to remove the sodium hydroxide. At this point, the hydrolyzed gel was swollen and diffracted in the red or infrared region. About 50 mg of 5-(biotinamido)pentylamine and about 100 mg of 1-(3-dimethylaminopropyl)-3-ethyl carbodiimide were dissolved in about 1.5 ml of water. The PCCA was immersed in this solution for about 8 hours. Following this period, the reaction products were washed out of the biotinylated gel with distilled water. The spectrum of the PCCA was measured to ensure that the diffraction wavelength was at or near the original blue. About 1 mg of an avidin labelled enzyme was then dissolved in about 1 ml of water; the biotinylated gel was immersed in this solution for between about 3 and 6 hours.

Example 6

Figure 6:
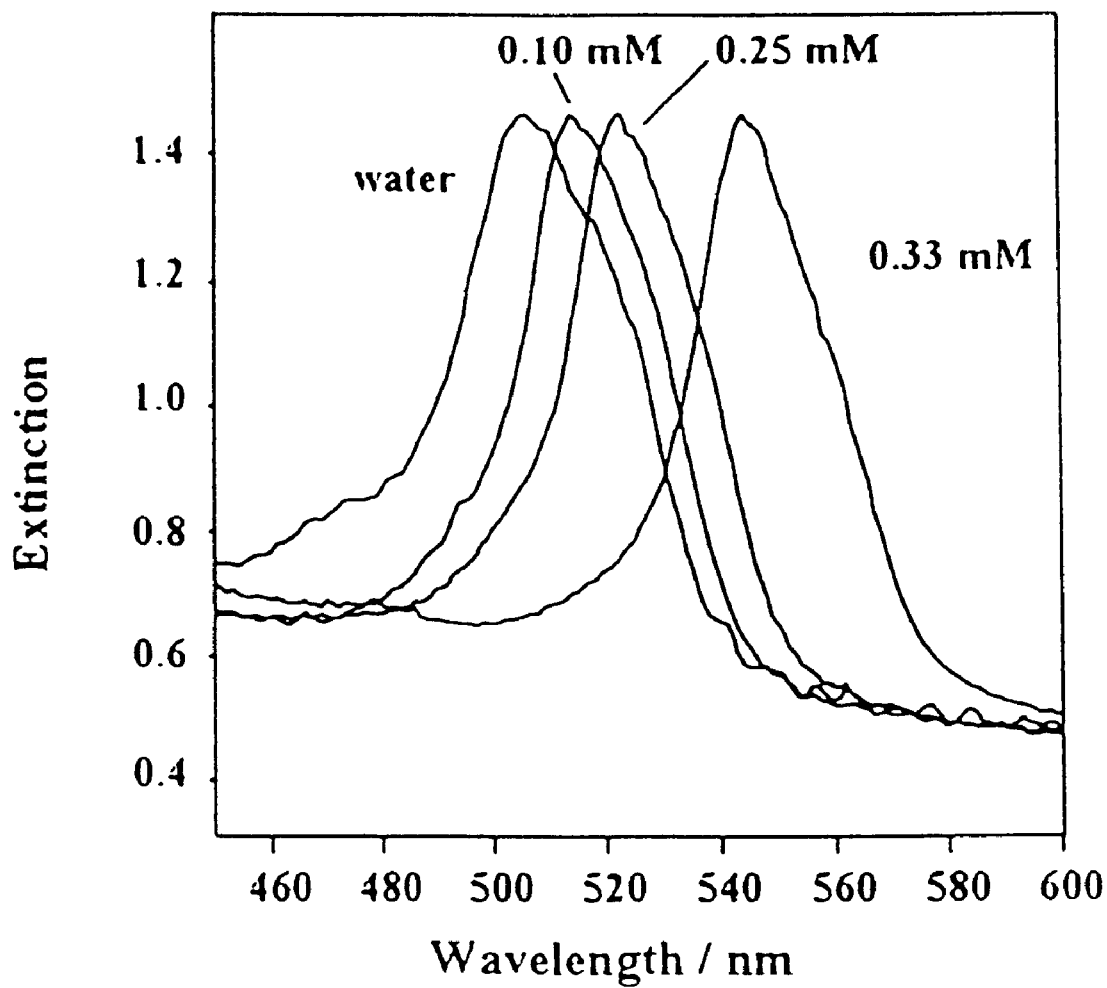
FIG. 6 shows the response of a PCCA to various concentrations of o-nitrophenyl-β-D-galactopyranoside, as determined according to the methods of Example 6.

The sensor device made according to Example 5, using β-D-galactosidase as the enzyme, was tested in various solutions of o-nitrophenyl-β-D-galactopyranoside ranging from 0.10 mM to 0.33 mM; water and sucrose were used as controls. As can be seen in FIG. 6, the wavelength diffracted in the water control was about 505 nm, in a 0.1 mM o-nitrophenyl-β-D-galactopyranoside solution was about 515 nm, in a 0.25 mM solution was about 525 and in a 0.33 mM solution was about 550; the change from 505 nm to 550 nm corresponds with a color shift from green to yellowish green at normal incidence. Diffracted wavelength was determined using a Perkin Elmer Lambda-9 spectrometer. These wavelength shifts demonstrate that the sensor devices of the present invention can be used to detect even small increases in sugar concentration. The sensor gave no response in either 0.1 or 0.2 mM of sucrose, thereby confirming that the enzyme specific reaction between o-nitrophenyl-β-D-galactopyranoside and β-D-galactosidase was causing the sensor response.

Example 7

Figure 7:
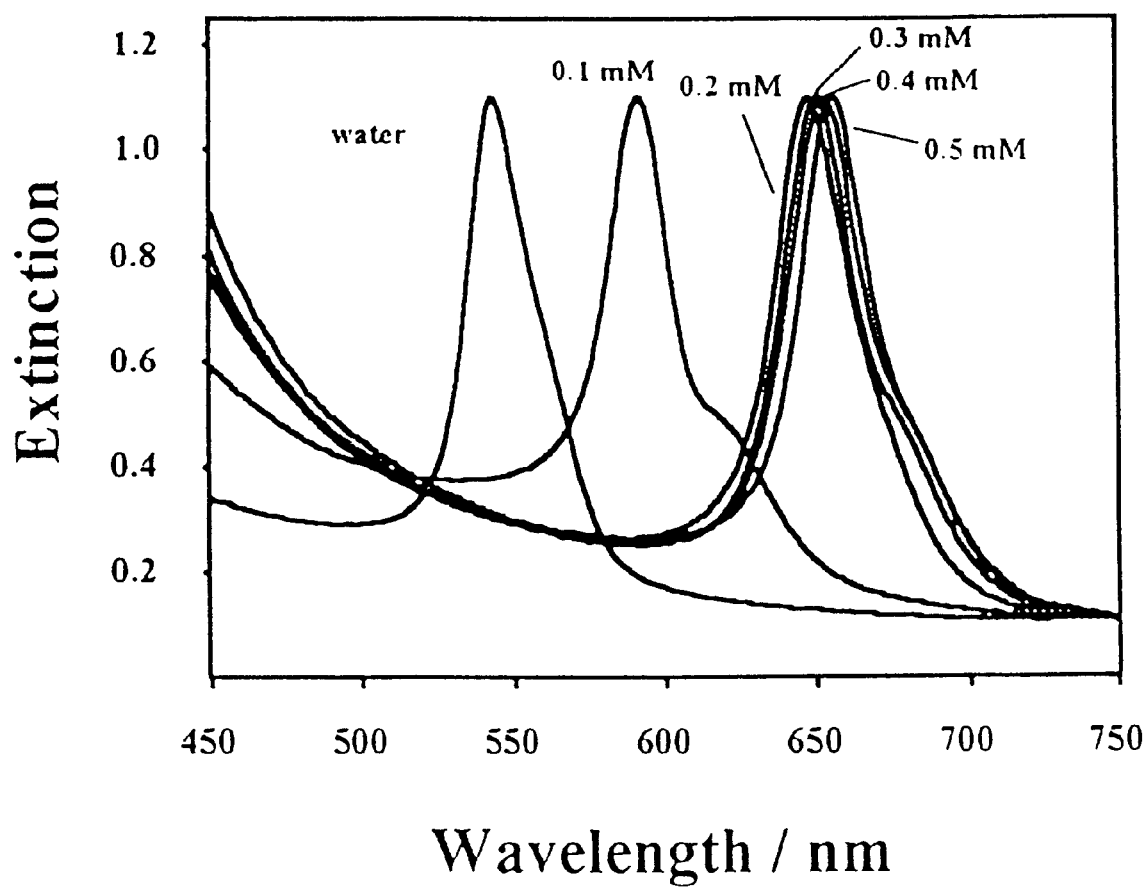
FIG. 7 illustrates the response of a PCCA in various glucose concentrations, as determined by the methods of Example 7.

The sensor device made according to Example 5, using glucose oxidase as the enzyme, was tested for reaction with various glucose-containing solutions. As can be seen in FIG. 7, the diffraction wavelength when the device was in water was approximately 550 nm. The diffracted wavelength, as measured by a Perkin Elmer Lambda-9 spectrometer, shifted to about 600 nm in a solution of 0.1 mM glucose, and to about 650 in the 0.2 mM through 0.5 mM solutions of glucose. Cleavage of the glucose by the glucose oxidase, when concentrations were at least 0.2 mM glucose, caused a wavelength shift of almost 100 nm, which corresponds to a color shift from yellowish green to deep red at normal incidence and was easily seen with the unaided human eye.

Example 8

Figure 8:
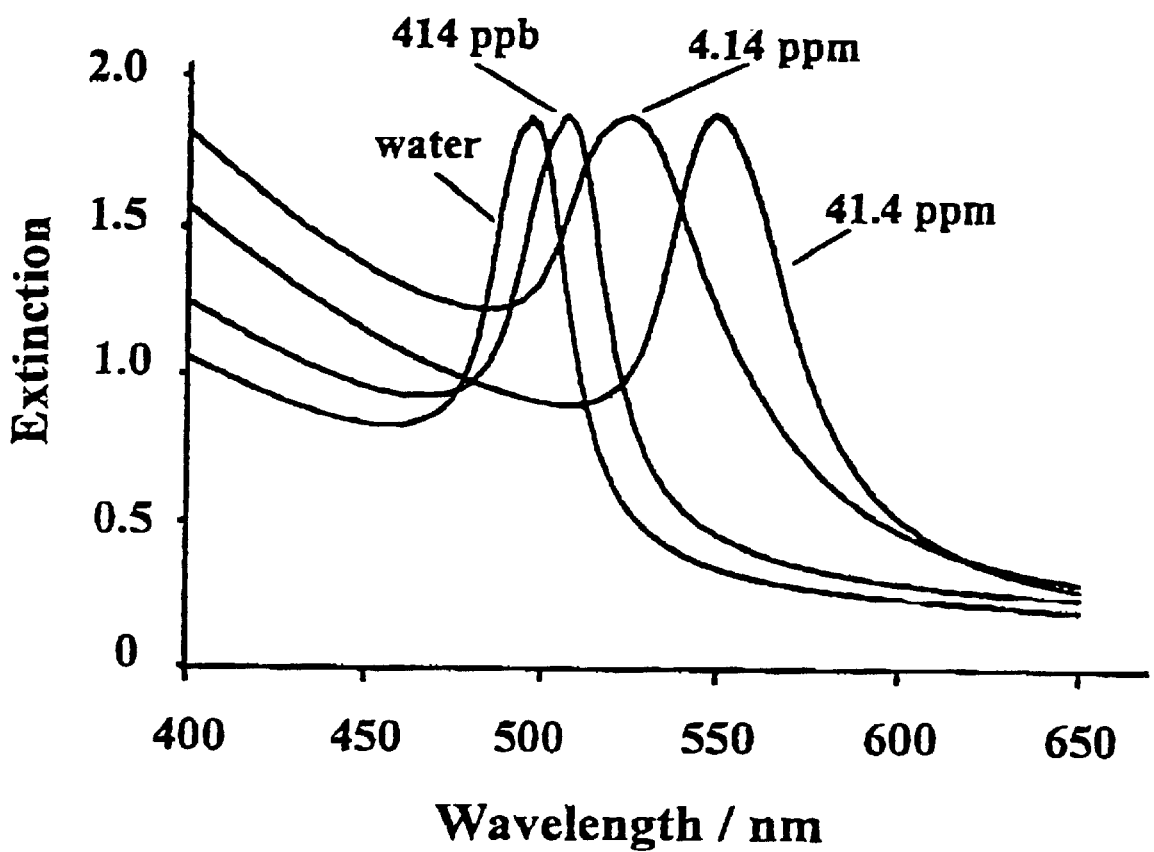
FIG. 8 illustrates the response of a PCCA in various lead concentrations, as determined by the methods of Example 8.

The response of the PCCA prepared as described in Example 1 to various lead concentrations was tested. Diffracted wavelength was determined using a Perkin Elmer Lambda-9 spectrometer. Water was used as a control. Crown ether binding of the lead ions localized the ion charges at the covalently bound crown ether groups. The resulting repulsive interactions caused the gel to swell, which in turn increases the diffracted wavelength. This can be seen in FIG. 8.

Example 9

Figure 9:
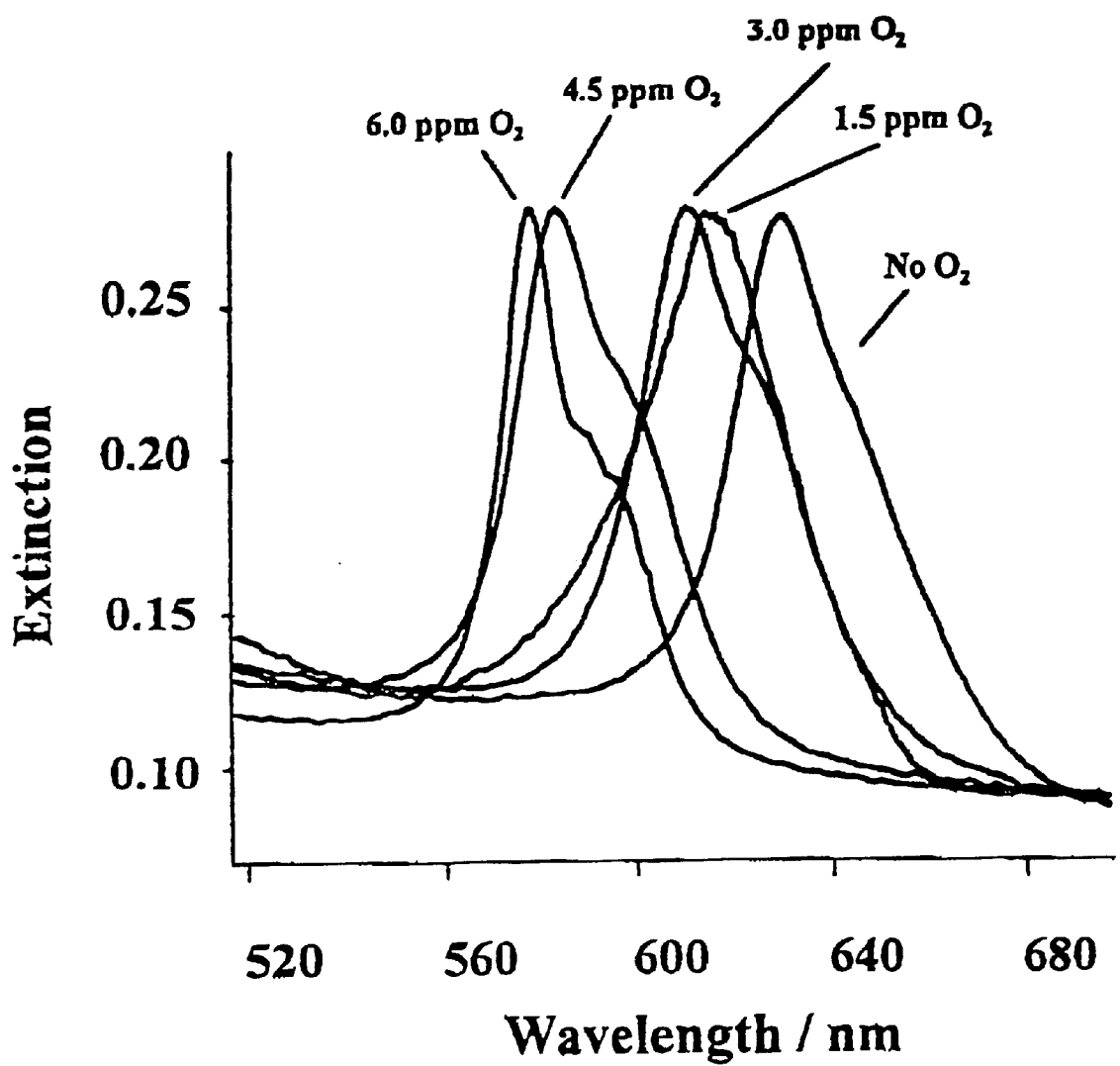
FIG. 9 illustrates the response of a PCCA in various concentrations of dissolved oxygen, in the presence of a constant glucose concentration, as determined by the methods of Example 9.

A sensor device was made according to the methods of Example 5, using glucose oxidase (GOx) as the enzyme. The glucose concentration was kept constant, at a volume of about 0.2 mM, to test the effects of dissolved oxygen on the PCCA. The results are presented in FIG. 9, which show the dissolved oxygen dependence of the diffraction wavelength of the film. Diffracted wavelength was determined using a Perkin Elmer Lambda-9 spectrometer. The PCCA was sensitive to oxygen levels between approximately 1.5 ppm and 6.0 ppm. Reoxidation of the flavin was believed to result in a shrinkage of the film, due to the reduction of electrostatic repulsion. This demonstrated that the swelling of the glucose sensor was due to the anionic reduced form of the enzyme as well as demonstrating the utility of the PCCA sensor for detection of gases in solution.

Whereas particular embodiments of this invention have been described above for purposes of illustration, it will be evident to those skilled in the art that numerous variations of the details of the present invention may be made without departing from the invention as defined in the appended claims.

What is claimed is:

1. A composition comprising a polymerized hydrogel that undergoes a volume change in response to a specific chemical stimulus, and a crystalline colloidal array of charged particles having a lattice spacing, the array embedded in the hydrogel, wherein the hydrogel includes a chemical stimulus recognition component capable of recognizing the specific chemical stimulus, which component is selected from the group consisting of crown ethers, cyclodextrins, calixarenes, biomolecular recognition components, and chelating agents; and further wherein the crystalline colloidal array has light diffracting properties and the volume change causes the lattice spacing to change thereby causing the light diffracting properties to change.

2. The composition according to claim 1 wherein said hydrogel is comprised of a first comonomer that is a gel monomer, a second comonomer, comprising the chemical stimulus recognition component, and a cross-linking agent.

3. The composition according to claim 1 wherein said hydrogel is hydrophilic.

4. The composition according to claim 2 wherein said gel monomer is ion-free.

5. The composition according to claim 4 wherein said gel monomer is selected from the group consisting of acrylamide, purified agarose, N-vinylpyrolidine, and methacrylate.

6. The composition according to claim 4 wherein said gel monomer is N-isopropylacrylamide.

7. The composition according to claim 2 wherein the cross-linking agent is selected from the group consisting of N,N'-methylenebisacrylamide, methylenebis methacrylamide and ethyleneglycol-dimethacrylate.

8. The composition according to claim 2 wherein the hydrogel further comprises a third monomer.

9. The composition according to claim 8 wherein the third monomer is selected from the group consisting of acrylamide and substituted acrylamide.

10. The composition according to claim 1 wherein the chemical stimulus recognition component is selected from the group consisting of crown ethers, cyclodextrins and calixarenes.

11. The composition according to claim 1 wherein said chemical stimulus recognition component is 4-acylamidobenzo 18-crown-6 ether.

12. The composition according to claim 1 wherein the chemical stimulus recognition component is a biomolecular recognition component.

13. The composition according to claim 12 wherein said biomolecular recognition component is selected from the group consisting of enzymes, antigens, nucleic acids, nucleic acid sequences, amino acids, amino acid sequences, peptides, porphyrins, ferritins, pheromone receptors, and antibodies.

14. The composition according to claim 12 wherein the hydrogel is further comprised of a gel monomer component and one or more linking molecules, the linking molecules link said biomolecular recognition component to said gel monomer component.

15. The composition according to claim 14 wherein said linking molecule is 5-(biotinamido)pentylamine.

16. The composition according to claim 14 wherein said linking molecule is bound to a second linking molecule or to the gel monomer component.

17. The composition according to claim 16 wherein said linking molecule is avidin.

18. The composition according to claim 1 wherein the stimulus recognition component is a chelating agent.

19. The composition according to claim 1 wherein the volume change is between about 0.1 and 50%.

20. The composition according to claim 1 wherein the crystalline colloidal array is comprised of particles selected from the group consisting of colloidal polystyrene, polymethylmethacrylate, silicon dioxide, aluminum oxide, poly tetrafluoroethylene and poly N-isopropylacrylamide.

21. The composition according to claim 1 wherein the chemical stimulus is selected from the group consisting of lead ions, potassium ions and sodium ions.

22. The composition according to claim 1 wherein the hydrogel comprises more than one polymer network, the polymer networks interpenetrating each other.

23. The composition according to claim 22 wherein one of the polymer networks comprises the stimulus recognition component.

24. The composition according to claim 23 wherein said stimulus recognition component is selected from the group consisting of crown ethers, cyclodextrins, and calixarenes.

25. The composition according to claim 24 wherein said stimulus recognition component is 4-acrylamidobenzo 18-crown-6 ether.

26. The composition according to claim 22 wherein the array is comprised of particles selected from the group consisting of colloidal polystyrene, polymethacrylate, silicon dioxide, aluminum oxide, polytetrafluoroethylene and poly N-isopropylacrylamide.

27. The composition according to claim 26 wherein at least one of said polymer networks is comprised of a gel monomer, the gel monomer is selected from the group consisting of acrylamide, purified agarose, N-vinyl pyrolidine and methacrylate.

28. The composition according to claim 22 wherein the hydrogel is hydrophilic.

29. The composition according to claim 22 wherein at least one of said polymer networks is comprised of gel monomer, the gel monomer being ion-free.

30. The composition according to claim 29 wherein the gel monomer is N-isopropylacrylamide.

31. The composition according to claims 22 wherein the volume change in response to the specific chemical stimulus is between about 0.1% and 50%.

32. A composition comprising a polymerized hydrogel that undergoes a volume change in response to a specific chemical stimulus, a crystalline colloidal array of charged particles having a lattice spacing, which array is embedded in the hydrogel, and a material, embedded within said hydrogel, which is released by said change in volume; wherein the crystalline colloidal array has light diffracting properties and the volume change causes the lattice spacing to change thereby causing the light diffracting properties to change.

33. A composition comprising a polymerized hydrogel that undergoes a volume change in response to a specific chemical stimulus, and a crystalline colloidal array of charged particles having a lattice spacing, which array is embedded in the hydrogel, wherein the chemical stimulus is selected from the group consisting of lead ions, potassium ions, and sodium ions; wherein the crystalline colloidal array has light diffracting properties and the volume change causes the lattice spacing to change thereby causing the light diffracting properties to change.

* * * * *